United States Patent [19]

Hagen et al.

[11] Patent Number: 4,717,416

[45] Date of Patent: Jan. 5, 1988

[54] 3,7-DICHLORO-8-QUINOLINE DERIVATIVES, AND THEIR USE FOR CONTROLLING UNDERSIRABLE PLANT GROWTH

[75] Inventors: Helmut Hagen, Frankenthal; Rolf-Dieter Kohler, Edingen-Neckarhausen; Juergen Markert, Mutterstadt; Bruno Wuerzer, Otterstadt, all of Fed. Rep. of Germany

[73] Assignee: BASF Aktiengesellschaft, Ludwigshafen, Fed. Rep. of Germany

[21] Appl. No.: 520,080

[22] Filed: Aug. 3, 1983

[30] Foreign Application Priority Data

Aug. 5, 1982 [DE] Fed. Rep. of Germany ....... 3229175

[51] Int. Cl.⁴ ..................... A01N 43/42; C07D 215/20
[52] U.S. Cl. ........................................ 71/94; 546/174; 546/176

[58] Field of Search ................ 542/417; 546/176, 174; 71/94

[56] References Cited

U.S. PATENT DOCUMENTS

| | | | |
|---|---|---|---|
| 2,427,286 | 9/1947 | Knapp et al. | 514/311 |
| 2,661,276 | 12/1953 | Schlesinger et al. | 71/94 |
| 2,924,604 | 2/1960 | Steinhards et al. | 71/94 |
| 3,279,907 | 10/1966 | Linder et al. | 71/94 |
| 4,497,651 | 2/1985 | Hagen et al. | 546/180 |

FOREIGN PATENT DOCUMENTS

| | | |
|---|---|---|
| 2322143 | 5/1973 | Fed. Rep. of Germany . |
| 1419788 | 12/1975 | United Kingdom . |
| 1424359 | 2/1976 | United Kingdom . |

*Primary Examiner*—Glennon H. Hollrah
*Assistant Examiner*—D. B. Springer
*Attorney, Agent, or Firm*—Keil & Weinkauf

[57] ABSTRACT

3,7-Dichloroquinoline derivatives which are substituted in the 8-position by —CH=CHR or —CH=NR$^5$, and their use for controlling undesirable plant growth.

7 Claims, No Drawings

3,7-DICHLORO-8-QUINOLINE DERIVATIVES, AND THEIR USE FOR CONTROLLING UNDERSIRABLE PLANT GROWTH

The present invention relates to 3,7-dichloro-8-quinoline derivatives, herbicides which contain these compounds as active ingredients and a method of controlling undesirable plant growth with these compounds.

German Laid-Open Application DOS No. 2,322,143, U.S. Pat. No. 2,661,276 and British Pat. No. 1,419,788 disclose quinoline derivatives having weak herbicidal properties.

We have found that 3,7-dichloro-8-quinoline derivatives of the formula

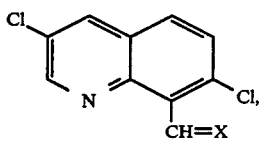

where
X is
(a) =CHR or
(b) =NR$^5$,
R is hydrogen, $C_1$–$C_8$-alkyl, unsubstituted or phenyl-substituted $C_2$–$C_6$-alkenyl, $C_1$–$C_6$-haloalkyl, $C_2$–$C_6$-haloalkenyl, cyano, or phenyl which is unsubstituted or substituted by one or more halogen atoms or nitro, methyl, methoxy or carboxyl radicals, or is unsubstituted or substituted furyl, thienyl, thiazolyl, imidazolyl, triazolyl, pyridyl, pyrimidinyl, pyridazinyl, pyrazinyl, benzthiazolyl, quinolinyl or benzoyl or the groups

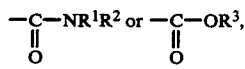

$R^1$, $R^2$ and $R^3$ are identical or different and are each hydrogen, unsubstituted or substituted $C_1$–$C_8$-alkyl, unsubstituted or substituted $C_2$–$C_6$-alkenyl, or phenyl which is unsubstituted or substituted by one or more halogen atoms or nitro, methyl, methoxy or carboxyl radicals, or is unsubstituted or substituted hetaryl, $R^5$ is amino, hydroxyl, ureido, thioureido, cyclohexyl, thiazolyl, imidazolyl, triazolyl, pyrimidinyl, pyridazinyl, pyrazinyl, thienyl, furyl, benzothiazolyl or anilino, where the phenyl radical can be substituted by one or more halogen atoms or nitro, methyl, methoxy, hydroxyl, carboxyl or dialkylamino groups, or $R^5$ is

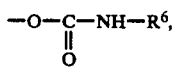

and $R^6$ is $C_1$–$C_8$-alkyl or is phenyl which is unsubstituted or substituted by one or more halogen atoms or nitro, methyl, methoxy or dialkylamino groups or is cyclohexyl, possess remarkable herbicidal actions and are tolerated by crops. Thus, the compounds (Ia) are useful, for example, for effectively controlling weeds of the genera Echinochloa and Galium. A particular feature of compounds (Ib) is their selective action. Preferred compounds of the formula I are those in which X is =NR$^5$.

In the novel 3,7-dichloro-8-quinoline derivatives, whose common feature is the —CH= group in the 8-position, the unsubstituted or halogen-substituted alkyl and alkenyl radicals can be straight-chain or, if permitted by the number of carbon atoms, branched. Preferred radicals are those of not more than 4 carbon atoms. Among the halogen atoms, chlorine and bromine are preferred to fluorine. Examples include methyl, ethyl, propyl, isopropyl and butyl. Aryl is primarily phenyl and may furthermore be naphthyl.

The present invention furthermore relates to processes for the preparation of the 3,7-dichloro-8-quinoline derivatives.

In one process, a 3,7-dichloro-8-phosphoniummethyl-quinoline of the formula II is reacted with an aldehyde of the formula III is accordance with the following equation:

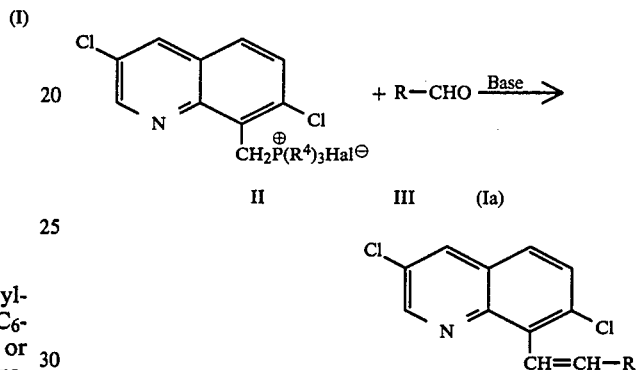

In these formulae, $R^4$ is phenyl or alkyl, Hal is chlorine, bromine or iodine and R has the above meanings.

In another process for the preparation of the 3,7-dichloro-8-quinoline derivatives of the formula (Ia), a 3,7-dichloro-8-formylquinoline of the formula IV is reacted with a phosphonium salt of the formula V, in accordance with the following equation:

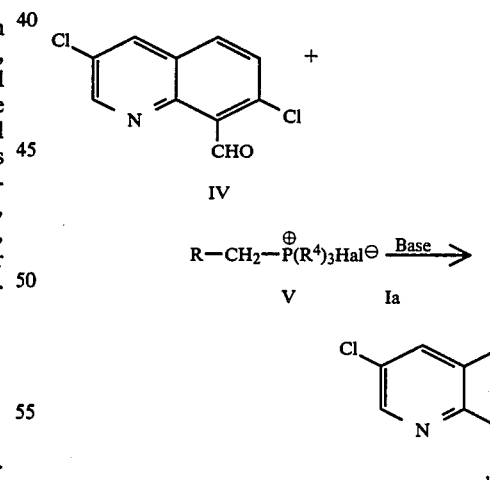

In these formulae, $R^4$ is phenyl or alkyl, Hal is chlorine, bromine or iodine and R has the above meanings.

Examples of suitable bases are sodium hydroxide, potassium hydroxide, alcoholates, such as sodium methylate, sodium ethylate, potassium ethylate and potassium tert.-butylate, amines, such as pyridine and N-methylmorpholine, sodium hydride and sodium amide. Sodium methylate is preferably employed.

The reaction is advantageously carried out in solvents or diluents which are inert to the reactants. Examples of suitable solvents or diluents are alcohols, eg. methanol, ethanol, propanols and butanols, ethers, eg. tetrahydrofuran, dioxane and diglycol dimethyl ether, aromatic hydrocarbons, eg. toluene, xylenes and chlorobenzenes, nitriles, eg. acetonitrile and propionitrile, dimethylformamide and dimethylsulfoxide, as well as mixtures of these solvents and diluents.

To carry out the processes, the starting materials and bases are usually employed in equimolar amounts. Advantageously, the starting materials are initially taken in a solvent, eg. ethanol, and the base, eg. sodium methylate, is added. An excess of one or other of the reactants can be advantageous in some cases.

The reaction temperature can be varied within a relatively wide range, and is in general from 0° to 100° C., preferably from 20° to 50° C.

The compounds of the formula (Ib) can be prepared by reacting the aldehyde of the formula

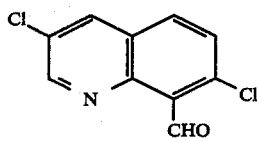 (V)

with an amine of the formula

 (VI).

In this formula, $R^7$ is amino, hydroxyl, benzothiazolyl, ureido, thioureido, cyclohexyl, thiazolyl, imidazolyl, triazolyl, pyrimidinyl, pyridazinyl, pyrazinyl, thienyl, furyl or anilino, and the phenyl radical can be unsubstituted or substituted by one or more halogen atoms or nitro, methyl, methoxy or dialkylamino groups.

The reaction is carried out in a suitable solvent, such as an alcohol, dimethylformamide, dimethylsulfoxide or dioxane, at from room temperature to 150° C., preferably from 80° to 120° C., the course of from 1 to 20, preferably from 2 to 6, hours.

Where the compound of the formula VI is a salt, this is either converted, before the reaction, to its free base, for example with an alcoholate, an alkali metal hydroxide, triethylamine or carbonate, or is reacted in the form of the salt, a suitable base, eg. an alcoholate, triethylamine, a hydroxide or a carbonate, being present in the reaction medium.

The oxime-carbamates of the formula I in which X is

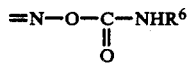

can be prepared by a method wherein 3,7-dichloroquinoline-8-aldoxime is reacted in a conventional manner with an isocyanate of the formula

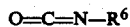 (VII)

in a suitable solvent, such as dimethylformamide, dimethylsulfoxide, dioxane or toluene. $R^6$ has the above meanings.

The aldehyde of the formula IV is obtained by hydrolyzing 3,7-dichloro-8-dichloromethylquinoline with sulfuric acid in a conventional manner. 3,7-dichloro-8-dichloromethylquinoline is obtained by chlorinating 7-chloro-8-methylquinoline, 7-chloro-8-chloromethylquinoline or 7-chloro-8-dichloromethylquinoline in dichlorobenzene at from 150° to 160° C. In particular, this chlorination can be carried out in an inert solvent, such as a dichlorobenzene or a trichlorobenzene, in the presence of a free-radical initiator, eg. azoisobutyronitrile or benzoyl peroxide, in the absence of light and at from 140° to 190° C., preferably from 150° to 160° C.

The Examples which follow illustrate the preparation of the quinoline derivatives of the formula I.

EXAMPLE 1

3,7-Dichloro-8-[(5-methyl-1,3,4-thiadiazol-2-yl)-vinyl]-quinoline 18 ml of a 15% strength solution of sodium methylate in methanol were added dropwise to a mixture of 11.3 g of 3,7-dichloro-8-formylquinoline and 20.5 g of 5-methyl-2-triphenylphosphoniummethyl-1,3,4-thiadiazole chloride in 100 ml of ethanol. The mixture was stirred for 3 hours at 20° C., after which the precipitate was filtered off under suction, suspended in water and again filtered off under suction.

Yield: 9 g (56% of theory); mp.: 189° C.

$C_{14}H_9Cl_2N_3S$ (322): Calculated: C 52.2, H 2.8, Cl 22.0, N 13.0, S 9.9. Found: C 52.2, H 3.1, Cl 22.4, N 12.9, S 9.9.

EXAMPLE 2

3,7-Dichloro-8-[(1-methyl-5-nitroimidazol-2-yl)-vinyl]-quinoline 36 ml of a 15% strength solution of sodium methylate in methanol were added dropwise, at 20° C., to a mixture of 50.6 g of 3,7-dichloro-8-triphenylphosphoniummethylquinoline chloride and 15.5 g of 2-formyl-1-methyl-5-nitroimidazole. After 2 hours, the yellow solid was filtered off under suction, washed with water and dried.

Yield: 24 g (68% of theory); mp.: 218° C.

$C_{15}H_{10}Cl_2N_4O_2$ (349): Calculated: C 51.6, H 2.9, Cl 20.3, N 16.0, O 9.2. Found: C 52.0, H 3.1, Cl 20.8, N 15.4, O 9.1.

EXAMPLE 3

1,2-Bis-(3,7-dichloroquinol-8-yl)-ethene 18 ml of a 15% strength solution of sodium methylate in methanol were added dropwise, at room temperature, to a suspension of 25.4 g of 3,7-dichloro-8-triphenylphosphoniummethylquinoline chloride and 11.3 g of 3,7-dichloro-8-formylquinoline in 150 ml of ethanol. The mixture was stirred for 2 hours, after which the yellow precipitate was filtered off under suction, treated with water and again filtered off under suction.

Yield: 20 g (95% of theory); mp.: 240° C.

$C_{20}H_{10}Cl_4N_2$ (420): Calculated: C 57.1, H 2.4, Cl 33.8, N 6.7. Found: C 57.1, H 2.7, Cl 33.5, N 6.7.

EXAMPLE 4

3,7-Dichloro-8-vinylquinoline 18 ml of a 15% strength solution of sodium methylate in methanol were added to 25.4 g of 3,7-dichloro-8-triphenylphosphonium-methylquinoline chloride and 5.5 g of 30% strength formaldehyde solution in 150 ml of ethanol. The mixture was stirred for 1 hour at 20° C., after which the precipitate was filtered off under suction, suspended in water and again filtered off under suction.

Yield: 8 g (72% of theory); mp.: 74° C.

C$_{11}$H$_7$Cl$_2$N (224): Calculated: C 58.9, H 3.1, Cl 31.7, N 6.3.

Found: C 57.8, H 3.4, Cl 32.9, N 5.6.

EXAMPLE 5

3,7-Dichloro-8-ethoxyacryloylquinoline 36 ml of a 15% strength solution of sodium methylate in methanol were added dropwise, at 20° C., to a suspension of 22.6 g of 3,7-dichloro-8-formylquinoline and 38.4 g of ethoxycarbonylmethyl-triphenyl-phosphonium chloide in 200 ml of ethanol. The mixture was stirred for 3 hours, after which the precipitate was filtered off under suction, washed with water and dried.

Yield: 18 g (60% of theory); mp.: 116° C.

C$_{14}$H$_{11}$Cl$_2$NO$_2$ (296): Calculated: C 56.8, H 3.7, Cl 24.0, N 4.7, O 10.8. Found: C 55.9, H 3.6, Cl 24.4, N 4.9, O 11.4.

EXAMPLE 6

3,7-Dichloro-8-[2-(N-methyl-N-phenylcarbamyl)-vinyl]-quinoline 18 ml of a 15% strength solution of sodium methylate in methanol were added to 11.3 g of 3,7-dichloro-8-formylquinoline and 22.3 g of triphenylphosphoniumacetic acid N-methylanilide chloride in 150 ml of ethanol. The mixture was stirred for 4 hours, after which the precipitate formed was filtered off under suction, washed with water and dried.

Yield: 6 g (35% of theory); mp.: 172° C.

C$_{19}$H$_{14}$Cl$_2$N$_2$O (357): Calculated: C 63.9, H 3.9, Cl 19.9, N 7.8, O 4.5. Found: C 62.8, H 4.2, Cl 20.1, N 8.0, O 4.8.

EXAMPLE 7

3,7-Dichloro-8-[2-(2-chlorophenyl)-vinyl]-quinoline 25.4 g of 3,7-dichloro-8-triphenylphosphoniummethylquinoline chloride and 7.7 g of 2-chlorobenzaldehyde in 150 ml of ethanol were stirred, and 18 ml of a 15% strength solution of sodium methylate in methanol were added at 20° C. After 6 hours, the precipitate was filtered off under suction, washed with water and dried.

Yield: 15 g (89% of theory); mp.: 114° C.

C$_{17}$H$_{10}$Cl$_3$N (334.5): Calculated: C 61.0, H 3.0, Cl 31.8, N 4.2. Found: C 61.3, H 3.4, Cl 30.3, N 4.3.

EXAMPLE 8

3,7-Dichloro-8-(3-fluoro-4-methyl-4-tolylbuta-1,3-dienyl)quinoline 18 ml of a 15% strength solution of sodium methylate in methanol were added dropwise to a suspension of 25.4 g of 3,7-dichloro-8-triphenylphosphoniummethylquinoline and 8.9 g of 4-methyl-α-methyl-β-fluorocinnamaldehyde. The mixture was stirred for 16 hours at 20° C., after which the precipitate was filtered off under suction, washed with water and dried.

Yield: 16 g (86% of theory); mp.: 130° C.

C$_{21}$H$_{16}$FCl$_2$N (372): Calculated: C 67.7, H 4.3, F 5.1, Cl 19.1, N 3.8. Found: C 68.9, H 4.0, F 4.7, Cl 18.5, N 3.6.

EXAMPLE 9

3,7-Dichloro-8-[2-(4-hydroxybenzyl)-vinyl]-quinoline 36 ml of a 15% strength solution of sodium methylate in methanol were added to 11 g of 3,7-dichloro-8-formylquinoline and 21.6 g of 4-hydroxyacetophenone-triphenylphosphonium chloride in 150 ml of ethanol. The mixture was stirred for 2½ hours at 20° C., after which 3 ml of glacial acetic acid were added and the precipitate was filtered off under suction, washed with water and dried.

Yield: 12 g (70% of theory); mp.: >230° C.

C$_{18}$H$_{11}$Cl$_2$O$_2$N (344): Calculated: C 62.8, H 3.2, Cl 20.6, N 4.1, O 9.3. Found: C 62.7, H 4.0, Cl 20.7, N 4.1, O 8.9.

The 3,7-dichloro-8-quinoline derivatives listed in the Table below were prepared in a similar manner.

| No. | R | Mp. (°C.) |
|---|---|---|
| 10 | phenyl | 92 |
| 11 | 2,4-dichlorophenyl | 133 |
| 12 | 4-nitrophenyl | 203 |
| 13 | 3-nitrophenyl | 160 |
| 14 | 4-methoxyphenyl | 130 |
| 15 | 3-chloro-4-carboxyphenyl | >220 |
| 16 | furyl | 100 |
| 17 | 5-nitrofuryl | 138 |
| 18 | 5-nitrothienyl | 142 |

-continued

CH=CH—R

| No. | R | Mp. (°C.) |
|---|---|---|
| 19 | 2-pyridyl | 111 |
| 20 | 3-pyridyl | 142 |
| 21 | —C(=O)—NH—(2-chlorophenyl) | 240 |
| 22 | —C(=O)—NH—(2-COOCH₃-phenyl) | 192 |
| 23 | —C(=O)—NH—(2-COOH-phenyl) | >260 |
| 24 | —C(=O)—NH—(3-methyl-4-chlorophenyl) | >260 |
| 25 | —C(=O)—O—(2,4-dichlorophenyl) | 190 |
| 26 | —COOH | >260 |
| 27 | —CN | 180 |
| 28 | —C(=O)NH₂ | 190 |
| 29 | —CH=CH—phenyl | 124 |

EXAMPLE 30

177 parts of 7-chloro-8-methylquinoline and 1 part of azobisisobutyronitrile in 1,000 parts of dichlorobenzene were initially taken, and heated to 140° C. When this temperature was reached, the passage of 250 parts of chlorine into the mixture was begun. The temperature was increased to 160° C. When the reaction was complete, the solution was flushed with nitrogen, the major part of the solvent was distilled off, and the precipitated solid was filtered off under suction and washed with petroleum ether to give 255 parts (80% of theory) of 3,7-dichloro-8-dichloromethylquinoline of melting point 154° C.

EXAMPLE 31

56 parts of 3,7-dichloro-8-dichloromethylquinoline in 250 parts of 90% strength sulfuric acid were stirred for 6 hours at 100° C. The solution was cooled and then poured onto ice, and the precipitated solid was filtered off under suction, washed neutral with water and dried to give 39 parts (87% of theory) of 3,7-dichloroquinoline-8-carbaldehyde of melting point 208° C.

EXAMPLE 32

12 g of semicarbazide hydrochloride and 5.8 g of sodium methylate in 300 ml of ethanol were refluxed for 10 minutes, after which the mixture was cooled and the precipitated sodium chloride was filtered off under suction. 23 g of 3,7-dichloroquinoline-8-carbaldehyde were added to the filtrate, and the solution was stirred under reflux for 2 hours. The mixture was cooled, water was added, the precipitated product was filtered off under suction, washed with methanol and dried. The substance was recrystallized from dimethylformamide to give 22 g (78% of theory) of 3,7-dichloro-8-semicarbazonoquinoline of melting point >280° C.

EXAMPLE 33

23 g of 3,7-dichloroquinoline-8-carbaldehyde and 20 g of 2,4-dinitrophenylhydrazine in 500 ml of ethanol were heated at 80° C. for 5 hours. Water was added to the reaction mixture, and the precipitated solid was filtered off under suction and recrystallized from dimethylformamide to give 34 g (85% of theory) of 3,7-dichloro-8-(2,4-dinitrophenylhydrazono)-quinoline of melting point >280° C.

EXAMPLE 34

45 g of 3,7-dichloroquinoline-8-carbaldehyde and 10 g of hydrazinium hydroxide were suspended in 1,000 ml of ethanol, and the suspension was refluxed for 6 hours. The solvent was distilled off, ether was added to the greasy residue, and the solid was filtered off under suction and recrystallized from methoxypropanol to give 37 g (78% of theory) of 3,7-dichloroquinolinal-8-hydrazone of melting point 184° C.

EXAMPLE 35

22.6 g of 3,7-dichloroquinoline-8-carbaldehyde were dissolved in 300 parts of ethanol, 10.6 g of sodium carbonate and 6.9 g of hydroxylammonium chloride were added to this solution, and the suspension was refluxed for 1 hour. Thereafter, 1,000 g of water were added, and the precipitated solid was filtered off and dried to give 23 g (96% of theory) of 3,7-dichloro-8-hydroxyliminoquinoline of melting point 202° C.

EXAMPLE 36

24 g of 3,7-dichloroquinoline-8-aldoxime were dissolved in 250 ml of dimethylformamide, 12.5 g of cyclohexyl isocyanate were added dropwise at room temperature and the solution was then stirred at 50° C. for 5 hours. In the course of the reaction period, a further 12 g of cyclohexyl isocyanate were slowly added dropwise. 2 liters of water were added to the reaction solution, and the solid was filtered off under suction, suspended in a little methanol, again filtered off under suction and recrystallized from toluene with active carbon to give 26 g (72% of theory) of 3,7-dichloroquinoline-8-aldoxime cyclohexylcarbamate of melting point 152° C.

EXAMPLE 37

22.5 g of 3,7-dichloroquinoline-8-carbaldehyde, 10.5 g of sodium carbonate and 13 g of hydrazinium sulfate were added to 300 ml of ethanol, and the mixture was refluxed for 5 hours. The solution was cooled, and the solid was filtered off under suction, washed with water and recrystallized from dimethylformamide with active carbon to give 19 g (85% of theory) of di-(3,7-dichloro-8-quinolinal)-azine of melting point 208° C.

The following compounds may be prepared analogously.

| Ex. | $R^5$ | M.p. (°C.) |
|---|---|---|
| 38 | $-NH-C(=S)-NH_2$ | |
| 39 | cyclohexyl (H) | 96 |
| 40 | pyrimidin-2-yl (N=CH-CH=CH-N=) | |
| 41 | thiazol-2-yl (N=CH-CH=S-) | |
| 42 | 1H-1,2,4-triazol-3-yl (HN-N=CH-N=) | 240 |
| 43 | $-O-C(=O)-NH-CH(CH_3)_2$ | 132 |
| 44 | $-O-C(=O)-NH-C_6H_4(3\text{-}Cl)$ | 189 |
| 45 | $-O-C(=O)-NH-CH_3$ | 206 |
| 46 | $-O-C(=O)-NH-C_6H_3(2,3\text{-}Cl_2)$ | — |
| 47 | $-O-C(=O)-NH-C_6H_4(4\text{-}Cl)$ | — |
| 48 | $-O-C(=O)-NH-C_6H_3(2,5\text{-}Cl_2)$ | — |
| 49 | $-O-C(=O)-NH-C_2H_5$ | 145 |
| 50 | $-NH-C_6H_5$ | 90 |

The novel compounds (active ingredients) may be applied pre- or postemergence. In the case of especially sensitive crop plants, application techniques may be used in which the herbicidal agents are sprayed from suitable equipment in such a manner that the leaves of the sensitive crop plants are if possible not touched, and the agents reach the soil or the unwanted plants growing beneath the crop plants (post-directed, lay-by treatment).

The amount of active ingredient applied depends on the time of the year, the objective to be achieved, the plants to be combated, and the growth stage of the plants, and varies from approx. 0.1 to 5 kg/ha and more, but is preferably from 1 to 4 kg/ha. In the following, the excellent action and selectivity of the compounds according to the invention are illustrated with reference to only a few compounds.

The influence of the 3,7-dichloro-8-quinoline derivatives on the growth of unwanted and crop plants is demonstrated in greenhouse experiments.

The vessels employed were plastic flowerpots having a volume of 300 cm³, and which were filld with a sandy loam containing about 1.5% humus. The seeds of the test plants were sown shallow, and separately, according to species. Rice was grown in a peat-enriched substrate to ensure better growth. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare (Table 1) and 1.0 or 4.0 kg of active ingredient per hectare (Tables 4 to 7). After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment were 3.0 kg of active ingredient per hectare (Tables 2 and 3) and 1.0 kg of active ingredient per hectare (Tables 4 and 5).

The following test plants were used in the experiments:

| Botanical name | Common name |
| --- | --- |
| Avena sativa | oats |
| Beta vulgaris | sugarbeets |
| Brassica napus | rapeseed |
| Cassia tora | sicklepod |
| Echinochloa crus-galli | barnyardgrass |
| Euphorbia geniculata | South American member of the spurge family |
| Galium aparine | catchweed bedstraw |
| Oryza sativa | rice |
| Sesbania exaltata | hemp sesbania |
| Setaria italica | foxtail millet |
| Solanum nigrum | black nightshade |
| Sorghum bicolor | sorghum |
| Triticum aestivum | wheat |

The pots were set up in the greenhouse—species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

On preemergence application of 3.0 kg/ha, for example compounds nos. 4, 25 and 28 exhibited a considerable herbicidal action on *Echinochloa crus-galli*. Compounds nos. 4, 5 and 8, applied postemergence at the same rate, were effective against broadleaved plants such as *Cassia tora*.

Compounds nos. 14, 16 and 19, applied at a rate of 3.0 kg/ha, combated *Galium aparine* without damaging oats for example.

The greenhouse experiments further showed that compounds nos. 42 and 50, applied pre- and postemergence at a rate of 1.0 kg/ha, selectively combated unwanted plants in crops. This is also true of compound no. 32, applied preemergence at 1.0 kg/ha. In these experiments, compound no. 40, applied preemergence at a rate of 4.0 kg/ha, combated, for instance, broadleaved weeds in sugarbeets without damaging the latter.

In view of the good tolerance of the herbicides according to the invention, or agents containing them, by numerous broadleaved and other crops, and the numerous application methods possible, they may be used in a large number of crops for removing unwanted plant growth.

The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | parsley |
| Petroselinum crispum | |
| spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |

| Botanical name | Common name |
| --- | --- |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the novel 3,7-dichloro-8-quinoline derivatives may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE 1

Herbicidal action with reference to a species of unwanted grass; preemergence application in the greenhouse

| Compound (Example) no. | R | % damage to *Echinochloa crus-galli* at 3.0 kg/ha |
| --- | --- | --- |
| 28 | —C(=O)—NH₂ | 90 |
| 25 | 2,4-dichlorophenyl-C(=O)— | 100 |
| 4 | H | 100 |

TABLE 2

Herbicidal action with reference to an unwanted broadleaved plant; postemergence application in the greenhouse

| Compound (Example) no. | R | % damage to *Cassia tora* at 3.0 kg/ha |
| --- | --- | --- |
| 8 | —C(F)=C(CH₃)—(4-CH₃-phenyl) | 90 |
| 4 | H | 100 |
| 5 | —COOC₂H₅ | 100 |

TABLE 3

Selective control of broadleaved weeds in cereals with reference to catchweed bedstraw and oats; postemergence application in the greenhouse

| Compound (Example) no. | R | % damage to *Avena sativa* at 3.0 kg/ha | *Galium aparine* |
| --- | --- | --- | --- |
| 14 | 4-methoxyphenyl | 0 | 80 |
| 19 | pyridyl | 0 | 80 |
| 16 | furyl | 0 | 80 |

TABLE 4

Selective control of unwanted plant growth with compound no. 42; pre- and postemergence application in the greenhouse

| Test plants | Damage (%) at 1.0 kg/ha Preemergence | Postemergence |
| --- | --- | --- |
| *Oryza sativa* | 0 | 0 |
| *Triticum aestivum* | 0 | 0 |
| *Setaria italica* | 100 | 90 |
| *Solanum nigrum* | 95 | 95 |

TABLE 5

Selective control of broadleaved weeds with compound no. 50; pre- and postemergence application in the greenhouse

| Test plants | Damage (%) at 1.0 kg/ha Preemergence | Postemergence |
| --- | --- | --- |
| *Brassica napus* | 10 | 10 |
| *Oryza sativa* | 10 | 10 |
| *Cassia tora* | 98 | 100 |
| *Euphorbia geniculata* | 98 | 100 |
| *Sesbania exaltata* | 90 | 90 |
| *Galium aparine* | — | 95 |

TABLE 6

Control of broadleaved weeds in various crops with compound no. 32; preemergence application in the greenhouse

| Test plants | Damage (%) at 1.0 kg/ha |
| --- | --- |
| *Beta vulgaris* | 0 |
| *Brassica napus* | 0 |
| *Sorghum bicolor* | 0 |
| *Triticum aestivum* | 0 |
| *Euphorbia geniculata* | 100 |
| *Solanum nigrum* | 98 |

TABLE 7

Control of unwanted broadleaved plants in sugarbeets with compound no. 40; preemergence application in the greenhouse

| Test plants | Damage (%) at 4.0 kg/ha |
| --- | --- |
| *Beta vulgaris* | 0 |
| *Cassia tora* | 100 |
| *Euphorbia geniculata* | 95 |
| *Solanum nigrum* | 95 |

We claim:

1. A 3,7-dichloro-8-quinoline derivative of the formula

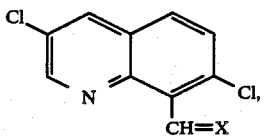

where

X is $=NR^5$ and $R^5$ is ureido or anilino.

2. 3,7-Dichloroquinoline-8-aldehyde phenylhydrazone.

3. A herbicidal composition for combatting unwanted grasses and broadleaved plants comprising from 0.1 to 95 wt% of a compound of claim 2, and inert additives.

4. A herbicidal composition for combatting unwanted grasses and broadleaved plants comprising a compound of the formula I as defined in claim 1, and inert additives.

5. The composition of claim 4 containing from 0.1 to 95 wt % of the compound of formula I.

6. A herbicidal composition for combatting unwanted grasses and broadleaved plants comprising from 0.1 to 95 wt % of the compound of the formula I as defined in claim 1, and inert additives.

7. A process for combatting the growth of unwanted grasses and broadleaved plants wherein the plants and/or soil are treated with a herbicidally effective amount of a compound of the formula I as defined in claim 1.

* * * * *